US009375285B2

(12) United States Patent
Crepaldi

(10) Patent No.: US 9,375,285 B2
(45) Date of Patent: Jun. 28, 2016

(54) INSTRUMENTS FOR STRETCHING AND/OR EXPANDING SKIN TISSUE

(75) Inventor: Pier Aldo Crepaldi, Livorno Ferraris (IT)

(73) Assignee: Herniamesh S.r.l., Chivasso, Turin (IT)

( * ) Notice: Subject to any disclaimer, the term of this patent is extended or adjusted under 35 U.S.C. 154(b) by 0 days.

(21) Appl. No.: 14/112,955

(22) PCT Filed: May 2, 2012

(86) PCT No.: PCT/IB2012/052189
§ 371 (c)(1),
(2), (4) Date: Oct. 21, 2013

(87) PCT Pub. No.: WO2012/150553
PCT Pub. Date: Nov. 8, 2012

(65) Prior Publication Data
US 2014/0046364 A1    Feb. 13, 2014

(30) Foreign Application Priority Data

May 3, 2011    (IT) .................. TO2011A0389

(51) Int. Cl.
*A61B 17/08*    (2006.01)
*A61B 19/00*    (2006.01)
*A61B 17/00*    (2006.01)

(52) U.S. Cl.
CPC .............. *A61B 19/24* (2013.01); *A61B 17/08* (2013.01); *A61B 2017/00862* (2013.01); *A61B 2017/081* (2013.01)

(58) Field of Classification Search
CPC .............. A61B 17/08–17/085; A61B 2017/08–2017/088
USPC .................................. 606/213, 216, 221
See application file for complete search history.

(56) References Cited

U.S. PATENT DOCUMENTS

| | | | | |
|---|---|---|---|---|
| 268,632 | A * | 12/1882 | Danforth | 606/218 |
| 2,743,497 | A * | 5/1956 | Davis | 24/196 |
| 2,919,481 | A * | 1/1960 | Finken et al. | 24/196 |
| 3,816,878 | A * | 6/1974 | Fulton et al. | 24/16 PB |
| 3,926,193 | A * | 12/1975 | Hasson | 606/218 |
| 3,971,384 | A * | 7/1976 | Hasson | 606/218 |
| 4,073,298 | A * | 2/1978 | Le Roy | A61B 17/08 |
| | | | | 606/216 |
| 4,366,604 | A * | 1/1983 | Anthony et al. | 24/323 |
| 4,535,772 | A * | 8/1985 | Sheehan | 606/218 |
| 5,972,006 | A * | 10/1999 | Sciaino, Jr. | 606/151 |
| 6,329,564 | B1 * | 12/2001 | Lebner | 602/41 |
| 2003/0163160 | A1 * | 8/2003 | O'Malley et al. | 606/213 |
| 2007/0021779 | A1 | 1/2007 | Garvin et al. | |
| 2007/0276437 | A1 * | 11/2007 | Call et al. | 606/232 |

FOREIGN PATENT DOCUMENTS

SU    1456109 A1    2/1989
WO    2010129863 A1    11/2010

* cited by examiner

*Primary Examiner* — Katherine Rodjom
*Assistant Examiner* — Jonathan Hollm
(74) *Attorney, Agent, or Firm* — Robert E. Alderson, Jr.

(57) ABSTRACT

Instruments are provided, representative embodiments of which have a first and a second jaw, from each of which at least one engaging element, whose distal end is suitable for engaging the skin tissue to be stretched, protrudes; an elastic member connecting the jaws, stressing them against each other when subjected to a traction force; and elements for adjusting the distance separating the jaws in the absence of traction force on the elastic member.

11 Claims, 4 Drawing Sheets

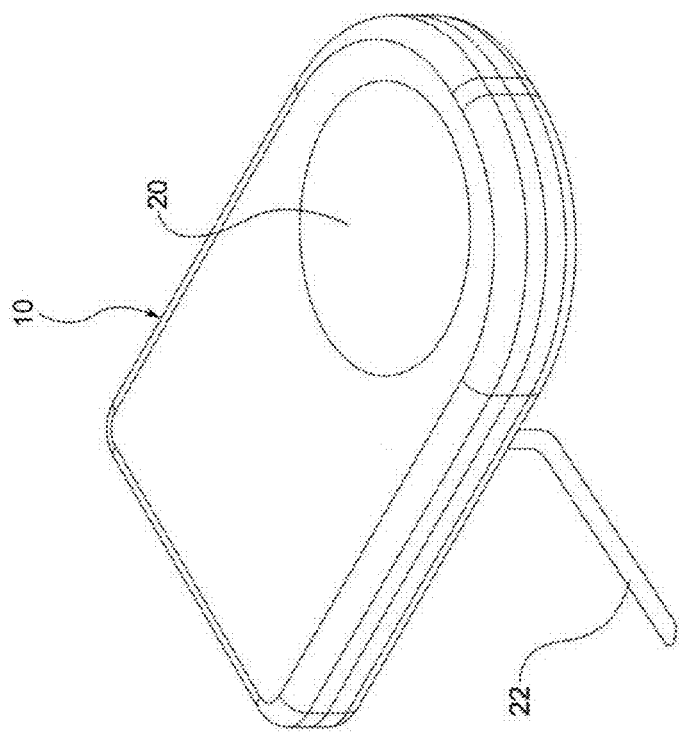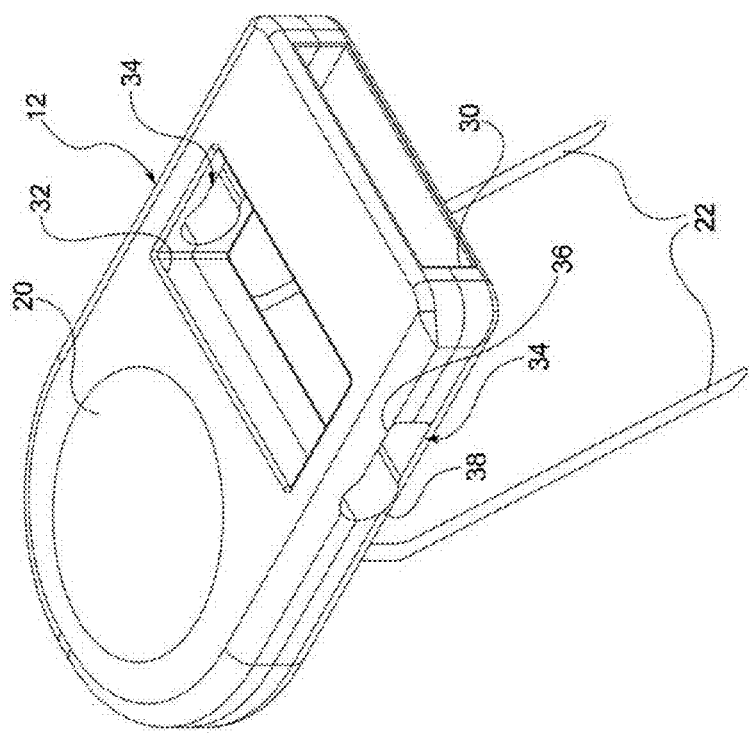
FIG. 2

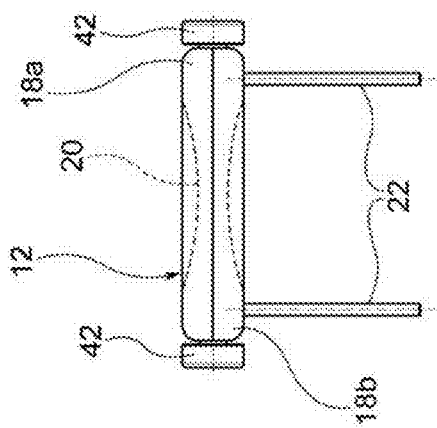
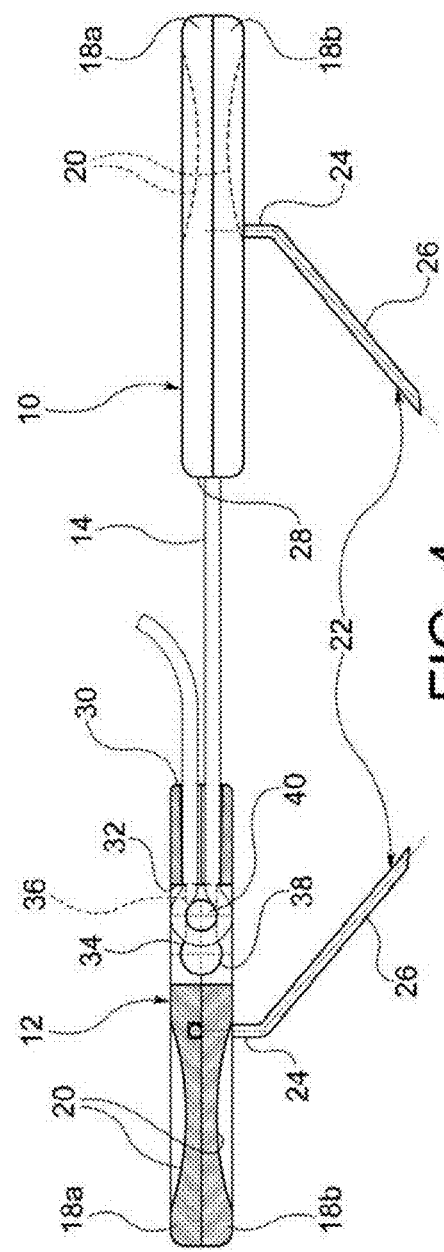
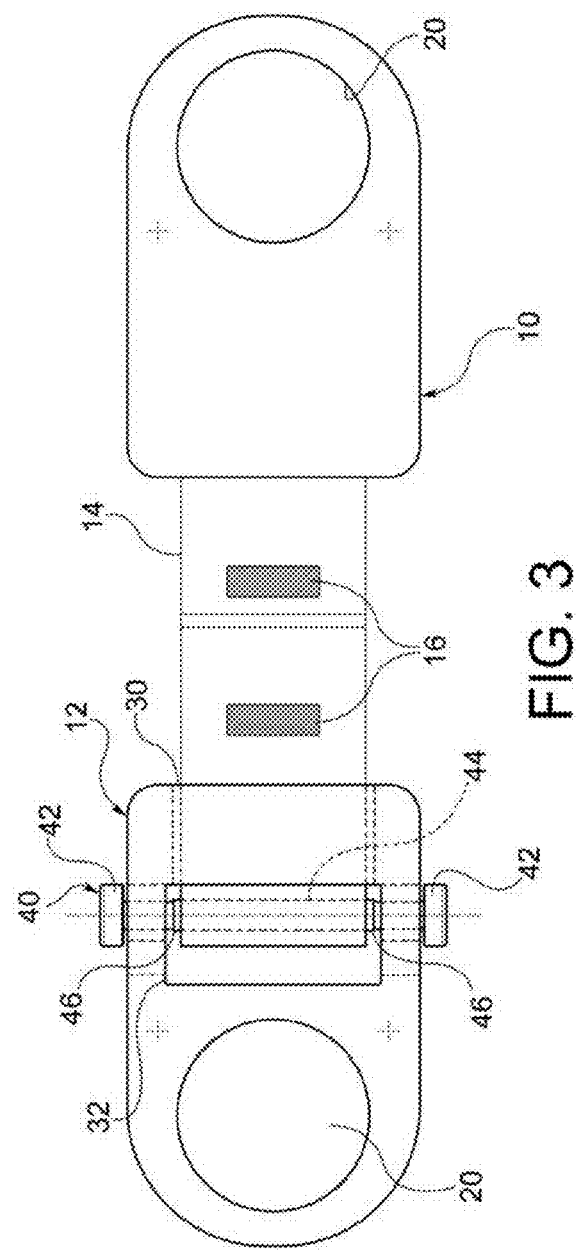

INSTRUMENTS FOR STRETCHING AND/OR EXPANDING SKIN TISSUE

CROSS-REFERENCE TO RELATED APPLICATIONS

This application is a National Phase Application of PCT International Application No. PCT/IB2012/052189, International Filing Date, May 2, 2012, claiming priority to Italian Patent Application No. TO2011A000389, filed May 3, 2011, each of which is hereby incorporated by reference in its entirety.

FIELD OF THE INVENTION

The present invention relates to an instrument for stretching/expanding skin tissue at the margins of ulcers and wounds in general, in particular for treating skin lesions, the margins of which, which can not be directly brought close, require second intention healing (growth of fresh tissue) with conversion into wounds which are suitable for first intention healing (stitching).

BACKGROUND OF THE INVENTION

Chronic skin lesions are an illness which is becoming more and more common, above all in first world countries, with percentages ranging from 0.4 to 1% of the population. The process for healing a chronic skin lesion (ulcer) is carried out in two ways: re-epithelialization and/or the growth of granulation tissue. The reparative process is also helped by a degree of contraction determined by the activity of the myofibroblasts. Another fact established from medical science is that a soft tissue subjected to traction or to load tends to extend (skin expanders, pendants for plastic surgery, etc.).

To guarantee an almost constant tension, known instruments of the type indicated above use rigid frames, which, by forcing the patient into a forced position, limit the quality of life to all intents and purposes.

US-2003/0163160, for example, describes a representative prior art device.

SUMMARY OF THE INVENTION

It is an object of the present invention to provide an instrument which is improved with respect to those in the prior art.

This object is achieved by instruments having the features described and claimed herein.

Owing to the means for adjusting the distance between the jaws in a non-stressed position, it is possible to adapt the instrument according to the invention to wounds of varying size, in particular wounds with an opening to be closed of between 5 and 30 cm or even greater. As a result, the instrument can be realized in one size, thus significantly reducing the inventory and logistical burden. The aforementioned adjustment of the distance between the jaws takes place, in a simple, quick and effective manner, by winding an end of the elastic member around the pivot and making it come out of the front fissure of the second jaw by a desired length.

At the same time, while ensuring this adjustment capacity, the instrument according to the invention has a simple and essential structure which makes it reliable, economical and versatile. In particular, the elastic member keeps the two jaws together, thereby preventing undesirable separation, even when the instrument is in a position of rest, and facilitating installation.

The instrument according to the invention makes it possible to reduce contraction times for wounds, bringing the margins of a lesion expanded down to deep levels close together to permit direct stitching. In particular, this is indicated for grade III-IV pressure ulcers, in accordance with the NPUAP-EPUAP scale, chronic wounds affecting subcutaneous adipose tissues and/or the fascia and/or the muscle of any etiology; grade III-IV lesions in accordance with the Wagner scale with a loss of substance of soft tissues in diabetic foot; dehiscence of surgical stitching of varying depth and extension; lacerated and contused wounds with margins which cannot be brought close together for direct stitching.

In association with medication products which are currently commercially available, the instrument according to the invention can be used broadly in all types of chronic or acute wounds which require long repair times or need plastic surgery; in this respect, unlike in the use of plastic edges, there is no loss of muscular-fascial structures for replenishing losses of substance, thus making it possible to preserve noble and moreover sound structures.

In addition, the instrument according to the invention has reduced dimensions, so as to reduce the discomfort caused to the patient and to allow the patient to also lie on the side of application and to move with a greater degree of freedom. This provides an improvement in the quality of life of the patient, avoiding the instigation of new lesions due to the fact that he/she cannot be mobilized.

Further advantages and features of the present invention will become evident from the detailed description which follows, given by way of non-limiting example and with reference to the appended drawings.

BRIEF DESCRIPTION OF THE FIGURES

FIG. 2 is a perspective view of two jaws of the instrument shown in FIG. 1, FIG. 3 is a plan view of the instrument according to the invention, FIG. 4 is a lateral elevated view, partially in section, of the instrument according to the invention, FIG. 5 is a view from the front of the instrument according to the invention.

DETAILED DESCRIPTION

Figure 1:
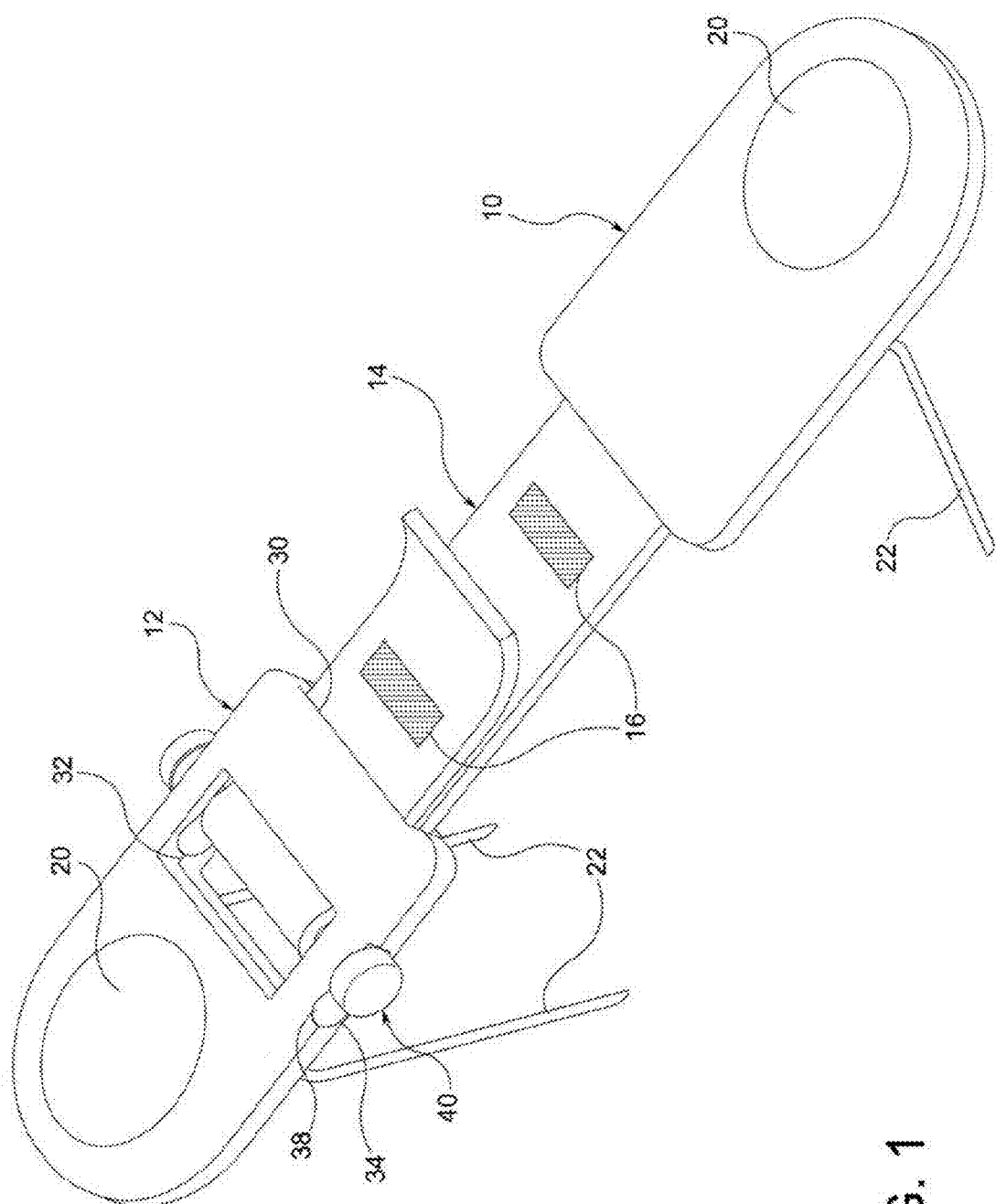
FIG. 1 is a perspective view of an instrument according to the invention.

An instrument for stretching skin tissue at the margins of ulcers, wounds and the like comprises a first and a second jaw 10, 12 connected by an elastic member, such as a strip 14 of elastomeric material, in particular silicone. The jaws 10, 12, which are connected by the strip 14, therefore face each other and are spaced apart from each other (see FIG. 1). The strip 14 has indicator marks 16 of the stress state, the function of which will be explained in detail hereinbelow.

Each jaw 10, 12 has a substantially flat body which is made of plastic material and is formed by two superimposed half members 18a, 18b which are joined by techniques which are conventional per se, for example by means of welding. The bodies of the jaws 10, 12 can be made of any plastic, or possibly even metallic, material which is not resorbable and is suitable for use in the medical field.

The major faces of the body of each jaw 10, 12 have a respective notch 20 to promote grip, and in addition two engaging elements, typically made of metal, protrude from the bottom major face, the distal ends of which engaging elements are designed for engaging in the skin tissues to be subjected to stretching. In particular, these engaging elements are shaped like needles 22 having a proximal portion 24 perpendicular to the body of the respective jaw 10, 12 and a distal portion 26 inclined with respect to the general plane of this body, advantageously at an angle of between 0° and 50°. The needles 22 may or may not be hollow on the inside.

The first jaw 10 has a front edge which faces towards the front edge of the second jaw 12 and has a socket 28 into which is inserted the first end of the strip 14, which is fixed permanently in said socket by conventional methods, for example by means of bonding or mechanical fastening devices.

The second jaw 12 has a front edge with a fissure 30 which faces towards the front edge of the first jaw 10. The mid portion of the body of the jaw 12 is provided with a through-opening 32, which communicates with the fissure 30 and has side edges in which respective slots 34 are present, by way of which the opening 32 communicates with the outside even at the sides of the body of the jaw 12. In embodiments of the invention which are not shown, the opening 32 may also not be a through-opening and thus affect only one face of the body of the jaw 12. Each slot 34 has a front portion 36 having a substantially rectangular section and a rear portion 38 having a rounded section which is larger than the front portion 36.

Figure 6:
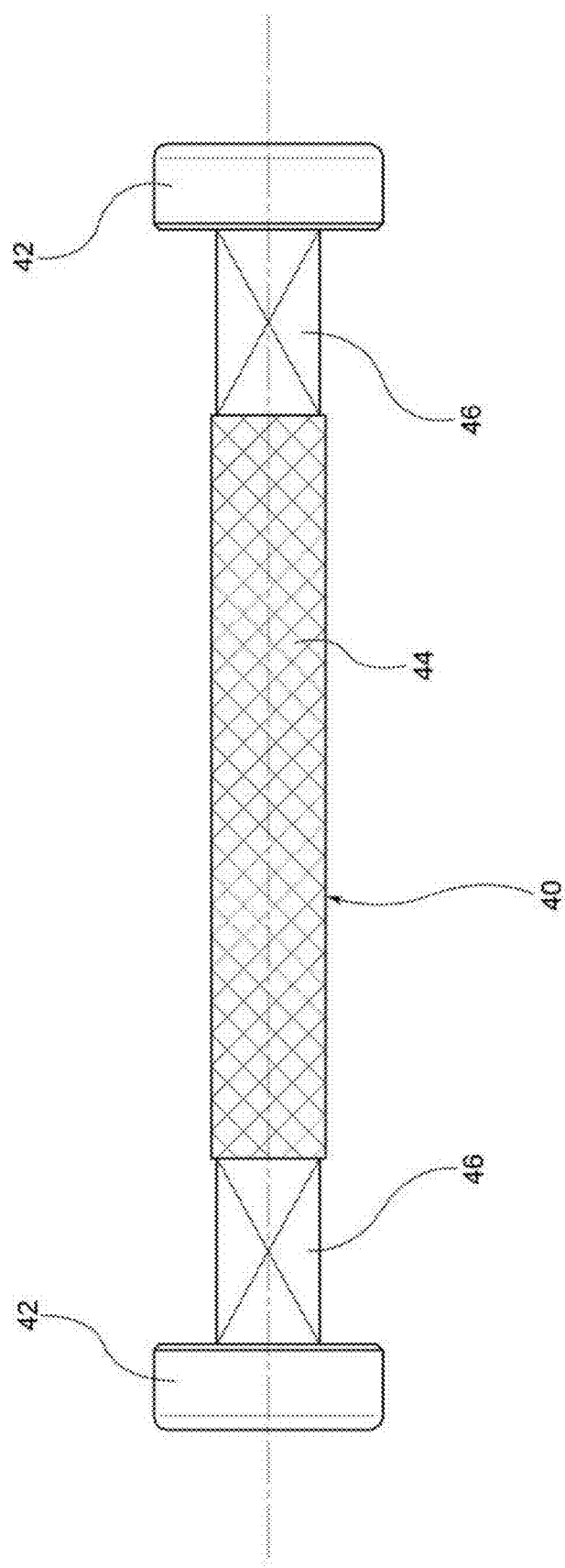
FIG. 6 is a view, on an enlarged scale, of a pivot which forms part of the instrument according to the invention.

A pivot 40 passes through the slots 34 and the opening 32, lying in the general plane of the body of the jaw 12 and perpendicularly with respect to the longitudinal axis of the strip 14. The pivot 40 (FIG. 6) has respective heads 42 at the ends, a mid portion 44 having a substantially circular cross section and intermediate portions 46 between the mid portion 44 and each head 42, having a cross section with sharp corners, in particular square corners. The intermediate portions 46 of the pivot 40 are placed in the respective slots 34, the mid portion 44 in the opening 32 and the heads 42 on the outside of the body of the jaw 12. The height of the intermediate portions 46 of the pivot 40 corresponds substantially to that of the front portion 36 of the slots 34, so as to make it possible for the pivot 40 to slide within the slots 34, but not to rotate, as will be described in detail hereinbelow.

The pivot 40 as a whole constitutes a single rigid body which can be monolithic or can be obtained by assembling a number of different parts, for example by inserting the distal ends of the intermediate portions 46 with an interference fit into cavities made in the respective heads 42. The pivot 40 can be made of any desired material suitable for use in the medical field.

The strip 14 is passed in the fissure 30, wound around the mid portion 44 of the pivot 40 and is again passed through the fissure 30, whereby the second end thereof freely protrudes from the second jaw 12.

This method for association of the strip 14 with the second jaw 12 makes it possible to continuously regulate the size of the instrument in accordance with the extension of the wound of which the margins have to be brought close together. For this purpose, it is necessary to position the pivot 40 such that the intermediate portions 46 thereof pass through the rear portions 38 of the slots 34 having an enlarged section. In this way, the pivot 40 can rotate freely about its own longitudinal axis, making it possible for the strip 14 to slide about the pivot 40 until—once the desired sliding corresponding to a certain distance between the jaws 10, 12 has been effected—the pivot 40 is moved forwards into the front portions 36 of the slots 34 in which it can no longer rotate. In this position, the strip 14 is locked between the pivot 40 itself and the front wall of the opening 32 above and below the fissure 30 and can no longer slide with respect to the pivot 40.

This effects a preliminary regulation of the distance which separates the jaws 10, 12 in a position of rest, adapting said distance to the size of the wound to be treated, and the instrument can be installed. For this purpose, the jaws 10, 12 are then pushed apart, so as to subject the strip 14 to a traction force, and the distal ends of the needles 22 are engaged in the skin tissues at the edges of the wound to be treated. The application of the correct traction force is made easier by the marks 16 placed on the strip 14. In the absence of traction, indeed, these marks 16 have a rectangular shape, which tends to become square under the action of force. The transformation of the shape of the marks 16 into a square—which can easily be detected by any operator—thus indicates that the traction to which the strip 14 is subjected is correct. The elastic return force exerted by the strip 14 is applied to the distal ends of the needles 22, which subject the tissues in which they are inserted to stretching, so as to make it easier for the margins of the wound to be brought close together.

In principle, therefore, the operation of the instrument according to the invention is based on the principle of extending a tissue subjected to stretching/expansion.

The use of the instrument is directed in particular to making it possible to directly close, by means of stitching, wounds of which the margins cannot be brought close together directly, disregarding the mobilization of edges by means of plastic surgery techniques.

Clearly, without departing from the principle of the invention, the details of construction and the embodiments may differ considerably from those described purely by way of example, without thereby departing from the scope of the invention as defined in the appended claims.

The invention claimed is:

1. An instrument for stretching and/or expanding skin tissue at the margins of skin lesions comprising:
    a first and a second jaw which have respective longitudinal axes and from each of which at least one engaging element, whose distal end is suitable for engaging said tissue, protrudes,
    a single elastic member associated with the instrument disposed between and connecting said jaws and having a longitudinal axis centrally arranged in said instrument wherein two symmetrical portions are defined, configured to urge the jaws against each other when subjected to a traction force, and
    elements for adjusting the distance separating said jaws in the absence of traction force on the elastic member,
    wherein said single elastic member has a first end fixed to the first jaw and a second end which is adjustably associated with the second jaw, and wherein said second jaw has a flat body and a front edge with a fissure facing a front edge of the first jaw, an opening, in at least one face perpendicular to said front edge of the flat body of the second jaw, communicating with said fissure and having side edges in which respective slots are present in the mid portion of the body, a pivot passing through said slots and said opening, and wherein the elastic member passes through the fissure, is wound around the pivot, and again passes through the fissure, whereby the second end of the elastic member protrudes from said fissure toward the first jaw to which the first end of the single elastic member is fixed, wherein the second jaw has only two major faces including a bottom major face facing the skin tissue, and wherein said first jaw, said second jaw and said single elastic member have coinciding longitudinal axes.

2. The instrument of claim 1, wherein said adjusting elements allow for a continuous adjustment of the distance separating said jaws along said coinciding longitudinal axes.

3. The instrument of claim 2, wherein said at least one engaging element is needle-shaped.

4. The instrument of claim 1, wherein said elastic member is in the form of a strip.

5. The instrument of claim 4, wherein said strip has indicator marks of the stress state.

6. The instrument of claim 1, wherein said first jaw has a substantially flat body and a front edge with a socket in which a first end of said elastic member is fixed.

7. The instrument of claim 6, wherein two engaging elements protrude from a face of the body of said first jaw.

8. The instrument of claim 1, wherein two engaging elements protrude from a face of the body of said second jaw.

9. The instrument of claim 1, wherein each of said slots has a front portion having a substantially rectangular section and a rear portion having a section larger than the front portion.

10. The instrument of claim 9, wherein said pivot has respective heads at the ends, a mid portion having a substantially circular cross section and intermediate portions between the mid portion and each head having a cross section with sharp corners, said intermediate portions being placed in the respective slot and said elastic member being passed in the fissure, wound around the mid portion of the pivot and being again passed through the fissure, whereby a second end thereof freely protrudes from the second jaw.

11. The instrument of claim 1, wherein said elastic member connects said jaws, keeping them facing and spaced apart from each other.

\* \* \* \* \*